United States Patent
Ono et al.

(10) Patent No.: US 10,478,176 B2
(45) Date of Patent: Nov. 19, 2019

(54) TISSUE LIGATING DEVICE

(71) Applicant: THE UNIVERSITY OF TOKYO, Tokyo (JP)

(72) Inventors: Minoru Ono, Tokyo (JP); Ichiro Sakuma, Tokyo (JP)

(73) Assignee: The University of Tokyo, Tokyo (JP)

(*) Notice: Subject to any disclaimer, the term of this patent is extended or adjusted under 35 U.S.C. 154(b) by 404 days.

(21) Appl. No.: 15/314,382

(22) PCT Filed: May 27, 2015

(86) PCT No.: PCT/JP2015/065288
§ 371 (c)(1),
(2) Date: Apr. 21, 2017

(87) PCT Pub. No.: WO2015/182671
PCT Pub. Date: Dec. 3, 2015

(65) Prior Publication Data
US 2017/0224329 A1    Aug. 10, 2017

(30) Foreign Application Priority Data

May 27, 2014  (JP) ................................ 2014-109480

(51) Int. Cl.
*A61B 17/04* (2006.01)
*A61B 17/122* (2006.01)

(52) U.S. Cl.
CPC ...... *A61B 17/0487* (2013.01); *A61B 17/0482* (2013.01); *A61B 17/0483* (2013.01);
(Continued)

(58) Field of Classification Search
CPC ............ A61B 17/0487; A61B 17/0482; A61B 17/0483; A61B 2017/0417; A61B 2017/0414
(Continued)

(56) References Cited

U.S. PATENT DOCUMENTS

| 773,317 | A | * | 10/1904 | Funke | ........................ A45F 3/22 5/122 |
| 3,353,232 | A | * | 11/1967 | Brownson | ............. B63B 35/817 114/253 |

(Continued)

FOREIGN PATENT DOCUMENTS

| JP | 2001-507972 A | 6/2001 |
| JP | 2013-94408 A | 5/2013 |

(Continued)

OTHER PUBLICATIONS

Extended European Search Report, dated Jan. 9, 2018, for European Application No. 15800128.9-1122, 9 pages.
(Continued)

*Primary Examiner* — Julian W Woo
(74) *Attorney, Agent, or Firm* — Seed Intellectual Property Law Group LLP

(57) ABSTRACT

A tissue ligating device comprises a first fixation part to which a base end part of a suture thread is fixed and a second fixation part configured to allow insertion of the suture thread therethrough and allow to be crimped so as to newly fix a part of the suture thread, and thereby to define a loop starting from the base end part, in a state after ligation of tissue is performed. The second fixation part includes a back side wall part, a front side wall part, and a curved wall part turning back from the back side wall part to the front side wall part. An end part of the front side wall part far from the curved wall part is inclined or curved towards a front side.

10 Claims, 11 Drawing Sheets

(52) U.S. Cl.
 CPC ............ *A61B 2017/0414* (2013.01); *A61B 2017/0417* (2013.01)

(58) Field of Classification Search
 USPC .......................................... 24/129 W, 115 A
 See application file for complete search history.

(56) References Cited

U.S. PATENT DOCUMENTS

| | | | | |
|---|---|---|---|---|
| 3,516,403 | A | * | 6/1970 | Cournut ............... A61F 6/18 128/840 |
| 3,881,475 | A | * | 5/1975 | Gordon ............... A61F 6/144 128/839 |
| 3,937,217 | A | * | 2/1976 | Kosonen ............ A61F 6/144 128/839 |
| D248,541 | S | * | 7/1978 | Oberg ..................... D8/372 |
| 5,372,604 | A | * | 12/1994 | Trott ............. A61B 17/0401 411/922 |
| 9,055,939 | B2 | * | 6/2015 | Fujisaki ......... A61B 17/0487 |
| 9,987,016 | B2 | * | 6/2018 | Fujii ............. A61B 17/0401 |
| 2003/0093091 | A1 | | 5/2003 | Paolitto et al. |
| 2004/0260344 | A1 | | 12/2004 | Lyons et al. |
| 2005/0107810 | A1 | * | 5/2005 | Morales ......... A61B 17/00234 606/143 |
| 2006/0135969 | A1 | * | 6/2006 | Assia ................ A61F 2/16 606/151 |
| 2011/0106155 | A1 | | 5/2011 | Theobald et al. |
| 2012/0165865 | A1 | | 6/2012 | Fujisaki et al. |
| 2014/0121681 | A1 | | 5/2014 | Fujii |

FOREIGN PATENT DOCUMENTS

| | | |
|---|---|---|
| WO | 98/30151 A1 | 7/1998 |
| WO | 99/59476 A1 | 11/1999 |
| WO | 2012/073944 A1 | 6/2012 |

OTHER PUBLICATIONS

Japanese Office Action, dated Feb. 2, 2018, for Japanese Application No. 2014-109480, 7 pages. (with English Translation).

* cited by examiner

TISSUE LIGATING DEVICE

TECHNICAL FIELD

The present invention relates to a device used in the field of medical treatment for ligating tissue.

BACKGROUND ART

In the field of medical treatment, the procedures of suturing and ligating tissue are very important in most surgical operations, have high degree of difficulty, and require a lot of skill.

Especially difficult in the procedures of suturing and ligating tissue is the action of knotting a suture thread and thereby forming a knot. If the knot loosens, the suture or ligation is released and that can cause a critical complication.

JP2012130669A discloses a tissue ligating device previously proposed by the present inventors. As shown in FIGS. 16 and 17, the tissue ligating device 100 includes a first fixation part 101 to which a base end part 201 of a suture thread 200 is fixed and a second fixation part 102 configured to allow insertion of the suture thread 200 therethrough and allow to be crimped so as to newly fix a part of the suture thread, and thereby to define a loop starting from the base end part 201, in a state after ligation of tissue is performed. A suture needle 202 is attached to a tip end part of the suture thread 200.

The second fixation part 102 includes a back side wall part 102B, a front side wall part 102F, and a curved wall part 102C turning back from the back side wall part 102B to the front side wall part 102F.

The tissue ligating device 100 further includes a third fixation part 103 arranged on the other side (back side) of the second fixation part 102 and configured to allow insertion of the suture thread 200 therethrough and allow to be crimped so as to newly fix a part of the suture thread, and thereby to define a loop starting from the base end part 201, in a state after ligation of tissue is performed.

The third fixation part 103 includes a symmetrical front side wall part 103SF that is symmetrical to the front side wall part 102F of the second fixation part with respect to the back side wall part 102B of the second fixation part and a symmetrical curved wall part 103SC turning back from the back side wall part 102B to the symmetrical front side wall part 103SF.

An example of usage of the above-described tissue ligating device 100 will be explained below with reference to FIGS. 18 to 24.

First, the suture needle 202 attached to the tip end part of the suture thread 200 is held by an operator by using a forceps or the like, and then stuck into a target tissue T1 around a wound part W as shown in FIG. 18, for example. Thereafter, as shown in FIG. 19, the suture needle 20 is pulled out from a target tissue T2 opposing the target tissue T1 across the wound part W. In this way, the suture thread 10 is extended through the target tissues T1 and T2 so that the wound part W can be sutured.

Subsequently, as shown in FIG. 20, the operator holds the suture thread 200 or the suture needle 202 with a forceps or the like, and guides a part of the suture thread 200 to let it pass through a region between the back side wall part 102B and the front side wall part 102F. The part of the suture thread 200 may also be guided to pass through a region between the back side wall part 102B and the symmetrical front side wall part 103SF instead of the region between the back side wall part 102B and the front side wall part 102F.

Here, in the tissue ligating device 100 disclosed in JP2012130669A, a part of the back side wall part 102B farther from the curved wall part 102C than the end part of the front side wall part 102F far from the curved wall part 102C protrudes towards the front side to form a step part 102S (see FIG. 16). With the existence of the step part 102S, even when the suture thread 200 is going to leave the region between the back side wall part 102B and the front side wall part 102F due to its elasticity or the like, the occurrence of such leaving is advantageously prevented.

Thereafter, as shown in FIG. 21, the tip end side of the suture thread 200 is pulled away from the target tissues T1 and T2, by which the first fixation part 101 fixed to the base end part 201 of the suture thread 200 approaches the target tissue T1 and is pressed against the target tissue T1. At the same time, the suture thread 200 extending through the target tissues T1 and T2 is tightened up and the target tissues T1 and T2 are pulled together to approach each other.

FIG. 22 shows the state of the tissue ligating device 100 at that time. As shown in FIG. 22, the suture thread 200 is extending through the region between the back side wall part 102B and the front side wall part 102F. After the suture thread 200 is tightened up sufficiently, as shown in FIG. 23, the operator crimps and deforms the symmetrical front side wall part 103SF and the front side wall part 102F with respect to the back side wall part 102B by using a forceps or the like, thereby newly fixing a part of the suture thread 200 and setting a loop starting from the base end part 201.

The tissue ligating device 100 in this state functions as a knot Kn of the suture thread 200. As shown in FIG. 24, the looped suture thread sutures the target tissues T1 and T2 together and closes the wound part W. The suture becomes more secure if the suturing procedure is performed while applying tension to the suture thread 200 by pulling the suture thread 200.

After the loop of the suture thread 200 starting from the base end part 201 is set, a redundant suture thread 200 is cut off by the operator. Thereafter, the removed suture thread 200 and the suture needle 202 are withdrawn to the outside of the body cavity.

SUMMARY OF THE INVENTION

The present inventors have extensively confirmed the usability of the tissue ligating device 100 disclosed in JP2012130669A in actual surgical operations. Meanwhile, the present inventors have felt that there is still room for improvement in the procedure of guiding the suture thread 200 to the region between the back side wall part 102B and the front side wall part 102F. Further, the present inventors have considered that such improvement leads to a remarkable reduction in the load on operators, and also in the load on patients.

The present inventors have collected information on tendencies of the suture thread 200 in actual surgical operations, operators' evaluations of the tissue ligating device 100, and so forth, and newly conceived of the configurations of the present invention as a result of trial and error. The present invention is especially useful in surgical operations in which the forceps, etc. can be moved only in a limited space.

The present invention provides a tissue ligating device used for ligating tissue, including a first fixation part to which a base end part of a suture thread is fixed and a second fixation part configured to allow insertion of the suture thread therethrough and allow to be crimped so as to newly fix a part of the suture thread, and thereby to define a loop starting from the base end part, in a state after ligation of tissue is performed. The second fixation part includes a back side wall part, a front side wall part, and a curved wall part turning back from the back side wall part to the front side wall part. An end part of the front side wall part far from the curved wall part is inclined or curved towards a front side. A part of the front side wall part other than the end part is formed in a shape like a flat plate.

According to the present invention, the end part of the front side wall part far from the curved wall part is inclined or curved towards the front side, by which the procedure of guiding the suture thread to the region between the back side wall part and the front side wall part is made very easy. This remarkably reduces the load on operators, and also the load on patients. Further, according to the present invention, the part of the front side wall part other than the end part is formed in a shape like a flat plate, and thus the procedure of crimping and deforming the flat plate-shaped part and newly fixing a part of the suture thread is very easy.

Preferably, the end part of the front side wall part is also formed in a shape like a flat plate, length of the end part of the front side wall part is 10 to 40% of length of the front side wall part, and the end part of the front side wall part is inclined with respect to the part of the front side wall part other than the end part by an angle in a range of 10 to 80 degrees. When these conditions are satisfied, the procedure of guiding the suture thread to the region between the back side wall part and the front side wall part becomes very easy.

Preferably, the end part of the front side wall part is formed in a shape like a curved surface with an arc-like cross section, length of the end part of the front side wall part is 10 to 40% of length of the front side wall part, and a curvature radius of the cross section of the end part of the front side wall part is in a range of 0.05 to 2.0 mm. When these conditions are satisfied, the procedure of guiding the suture thread to the region between the back side wall part and the front side wall part becomes very easy.

Preferably, the tissue ligating device further includes a third fixation part configured to allow insertion of the suture thread therethrough and allow to be crimped so as to newly fix a part of the suture thread, and thereby to define a loop starting from the base end part, in a state after ligation of tissue is performed. The third fixation part includes a symmetrical front side wall part that is symmetrical to the front side wall part of the second fixation part with respect to the back side wall part of the second fixation part and a symmetrical curved wall part turning back from the back side wall part to the symmetrical front side wall part. An end part of the symmetrical front side wall part far from the symmetrical curved wall part is inclined or curved towards a back side. A part of the symmetrical front side wall part other than the end part is formed in a shape like a flat plate. In this case, postural stability of the tissue ligating device is improved since the structure of the second fixation part and that of the third fixation part are symmetrical to each other. Operability is higher since both the second fixation part and the third fixation part are usable for the fixation of the suture thread.

The present invention also provides a tissue ligating device used for ligating tissue, including a first fixation part to which a base end part of a suture thread is fixed and a second fixation part configured to allow insertion of the suture thread therethrough and allow to be crimped so as to newly fix a part of the suture thread, and thereby to define a loop starting from the base end part, in a state after ligation of tissue is performed. The second fixation part includes a back side wall part, a front side wall part, and a curved wall part turning back from the back side wall part to the front side wall part. The back side wall part is longer than the front side wall part. A part of the back side wall part farther from the curved wall part than an end part of the front side wall part far from the curved wall part has a surface inclined or curved towards a front side.

According to the present invention, the part of the back side wall part farther from the curved wall part than the end part of the front side wall part far from the curved wall part is inclined or curved towards the front side, by which the procedure of guiding the suture thread to the region between the back side wall part and the front side wall part is made very easy. This remarkably reduces the load on operators, and also the load on patients.

Preferably, the part of the back side wall part farther from the curved wall part than the end part of the front side wall part far from the curved wall part has a surface rising towards the front side and a surface continuing to the rising surface and inclined or curved towards the front side. In this case, the suture thread can be prevented from leaving the rising surface.

Preferably, a part of the back side wall part closer to the curved wall part than the inclined surface or the rising surface is formed in a shape like a flat plate, and the inclined surface of the back side wall part is inclined with respect to the flat plate-shaped part of the back side wall part by an angle in a range of 10 to 80 degrees. When these conditions are satisfied, the procedure of guiding the suture thread to the region between the back side wall part and the front side wall part becomes very easy.

Preferably, the curved surface of the back side wall part is formed as a surface with an arc-like cross section, a part of the back side wall part closer to the curved wall part than the curved surface or the rising surface is formed in a shape like a flat plate, and a curvature radius of the cross section of the curved surface of the back side wall part is in a range of 0.05 to 2.0 mm. When these conditions are satisfied, the procedure of guiding the suture thread to the region between the back side wall part and the front side wall part becomes very easy.

Preferably, the tissue ligating device further includes a third fixation part configured to allow insertion of the suture thread therethrough and allow to be crimped so as to newly fix a part of the suture thread, and thereby to define a loop starting from the base end part, in a state after ligation of tissue is performed. The third fixation part includes a symmetrical front side wall part that is symmetrical to the front side wall part of the second fixation part with respect to the back side wall part of the second fixation part and a symmetrical curved wall part turning back from the back side wall part to the symmetrical front side wall part. The back side wall part is longer than the symmetrical front side wall part. A part of the back side wall part farther from the symmetrical curved wall part than an end part of the symmetrical front side wall part far from the symmetrical curved wall part has a surface inclined or curved towards a back side. In this case, postural stability of the tissue ligating device is improved since the structure of the second fixation part and that of the third fixation part are symmetrical to each other. Operability is higher since both the second fixation part and the third fixation part are usable for the fixation of the suture thread.

In the above inventions, the first fixation part is desired to be configured to allow a part of the suture thread to be fixed thereto as the base end part through insertion of the suture thread and crimping in a state before ligation of tissue is performed.

In the above inventions, the tissue ligating device is desired to further include a suture thread attached to the first fixation part. In this case, it is desirable that one end of the suture thread be provided with a suture needle.

MODE FOR CARRYING OUT THE INVENTION

Preferred embodiments of the present invention will be described in detail with reference to the attached drawings.

Figure 1:
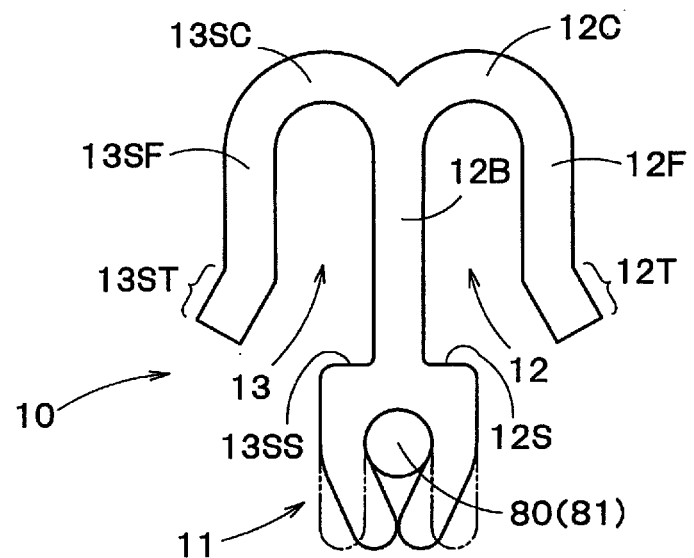
FIG. 1 is a schematic plan view showing a tissue ligating device in a first embodiment of the present invention.
Figure 2:
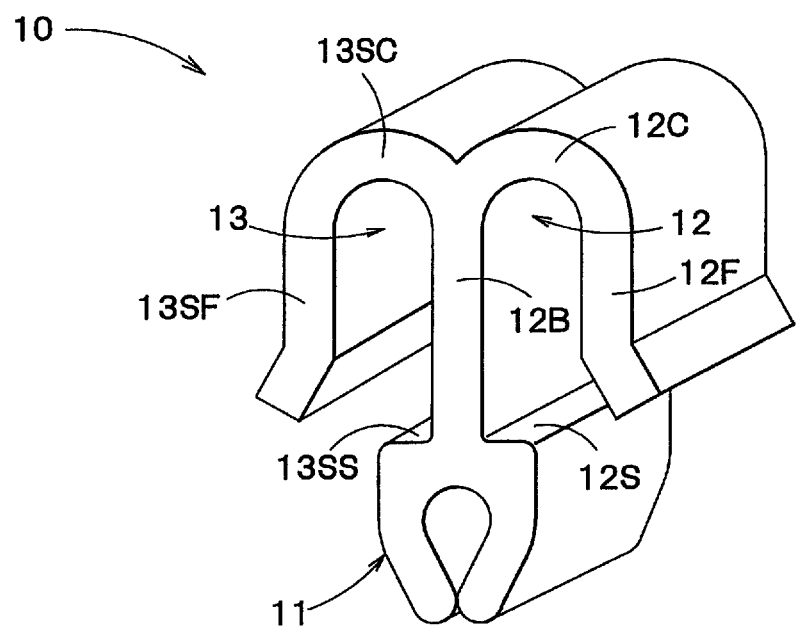
FIG. 2 is a schematic perspective view showing the tissue ligating device of FIG. 1.
Figure 3:
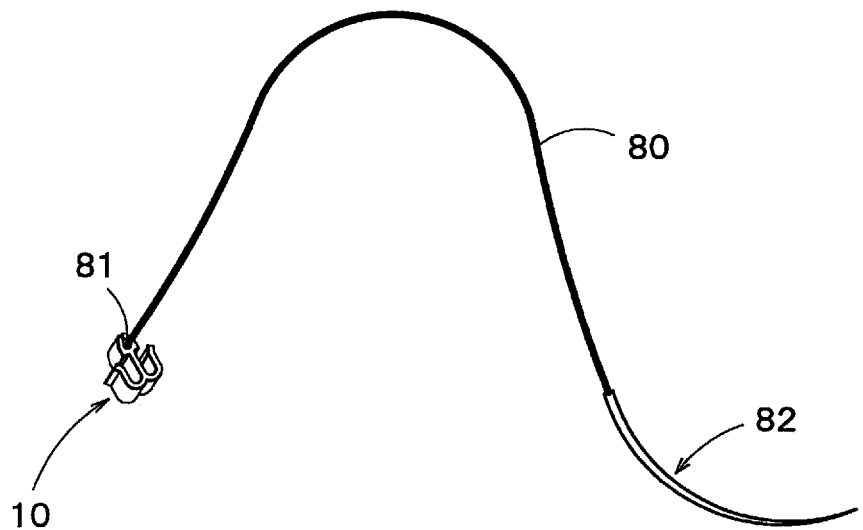
FIG. 3 is a schematic perspective view showing a state in which a suture thread has been fixed to a first fixation part of the tissue ligating device of FIG. 1.

FIG. 1 is a schematic plan view showing a tissue ligating device in a first embodiment of the present invention. FIG. 2 is a schematic perspective view showing the tissue ligating device of FIG. 1. FIG. 3 is a schematic perspective view showing a state in which a suture thread has been fixed to a first fixation part of the tissue ligating device of FIG. 1.

As shown in FIGS. 1 to 3, the tissue ligating device 10 in this embodiment includes a first fixation part 11 to which a base end part 81 of a suture thread 80 is fixed and a second fixation part 12 configured to allow insertion of the suture thread 80 therethrough and allow to be crimped so as to newly fix a part of the suture thread 80, and thereby to define a loop starting from the base end part 81, in a state after ligation of tissue is performed. A suture needle 82 is attached to a tip end part of the suture thread 80.

The first fixation part 11 in this embodiment is configured to allow insertion of the suture thread 80 therethrough and allow to be crimped, thereby to fix a part of the suture thread 80 as the base end part 81, in a state before ligation of tissue is performed. In FIG. 1, a state before the crimping is indicated by two-dot chain lines, while a state after the crimping is indicated by solid lines.

The second fixation part 12 in this embodiment includes a back side (left-hand side in FIG. 1) wall part 12B, a front side (right-hand side in FIG. 1) wall part 12F, and a curved wall part 12C turning back from the back side wall part 12B to the front side wall part 12F like a hair pin. An end part 12T of the front side wall part 12F far from the curved wall part 12C is inclined towards the front side.

Further, in the tissue ligating device 10 in this embodiment, a part of the back side wall part 12B farther from the curved wall part 12C than the end part of the front side wall part 12F far from the curved wall part 12C protrudes towards the front side to form a step part 12S.

The tissue ligating device 10 in this embodiment further includes a third fixation part 13 arranged on the other side (back side) of the second fixation part 12 symmetrically to the second fixation part 12 and configured to allow insertion of the suture thread 80 therethrough and allow to be crimped so as to newly fix a part of the suture thread 80, and thereby to define a loop starting from the base end part 81, in a state after ligation of tissue is performed.

The third fixation part 13 includes a symmetrical front side wall part 13SF that is symmetrical to the front side wall part 12F of the second fixation part with respect to the back side wall part 12B of the second fixation part and a symmetrical curved wall part 13SC turning back from the back side wall part 12B to the symmetrical front side wall part 13SF like a hair pin. An end part 13ST of the symmetrical front side wall part 13SF far from the symmetrical curved wall part 13SC is also inclined towards the back side.

Further, in the tissue ligating device 10 in this embodiment, a part of the back side wall part 12B farther from the symmetrical curved wall part 13SC than the end part of the symmetrical front side wall part 13SF far from the symmetrical curved wall part 13SC protrudes towards the back side to form a step part 13SS.

A usual biocompatible stainless steel may be used as the material of the tissue ligating device 10, but not limited thereto. Laser processing is usually used as the processing method for the tissue ligating device 10, but not limited thereto, other methods such as wire electrical discharge machining may also be used.

The size of the tissue ligating device 10 is generally as follows: the height in the vertical direction in FIG. 1 is approximately 0.8 to 1.6 mm; the width in the horizontal direction in FIG. 1 is approximately 0.3 to 1.0 mm; and the thickness in the direction orthogonal to the sheet of FIG. 1 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 10 of a relatively large size can be employed in cases of suturing a pancreatic duct (approximately φ5.0 mm) or a bile duct (approximately φ8.0 to 12.0 mm).

In this embodiment, a part of the front side wall part 12F other than the end part 12T is formed in a shape like a flat plate (thickness is approximately 0.06 to 0.10 mm). The end part 12T of the front side wall part 12F is also formed in a shape like a flat plate (thickness is also approximately 0.06 to 0.10 mm). A part of the symmetrical front side wall part 13SF other than the end part 13ST is also formed in a shape like a flat plate (thickness is approximately 0.06 to 0.10 mm). The end part 13ST of the symmetrical front side wall part 13SF is also formed in a shape like a flat plate (thickness is also approximately 0.06 to 0.10 mm). The back side wall part 12B is also formed in a shape like a flat plate (thickness is also approximately 0.06 to 0.10 mm).

The length of the end part 12T of the front side wall part 12F is approximately 20% of the length of the front side wall part 12F, but is not limited thereto. As for the proportion between sizes, the length of the end part 12T of the front side wall part 12F is desired to be 10 to 40% of the length of the front side wall part 12F. In this embodiment, the end part 12T of the front side wall part 12F is inclined by 30 degrees with respect to the part of the front side wall part 12F other than the end part 12T, but is not limited thereto. The inclination angle can be selected from a wide range of 10 to 80 degrees or a preferable range of 20 to 60 degrees.

Symmetrically, the length of the end part 13ST of the symmetrical front side wall part 13SF is approximately 20% of the length of the symmetrical front side wall part 13SF, but is not limited thereto. As for the proportion between sizes, the length of the end part 13ST of the symmetrical front side wall part 13SF is desired to be 10 to 40% of the length of the symmetrical front side wall part 13SF. In this embodiment, the end part 13ST of the symmetrical front side wall part 13SF is inclined by 30 degrees with respect to the part of the symmetrical front side wall part 13SF other than the end part 13ST, but is not limited thereto. The inclination angle can be selected from a wide range of 10 to 80 degrees or a preferable range of 20 to 60 degrees.

Resin or metal can be employed as the material of the suture thread 80. Materials having a certain level of elasticity to maintain straight condition are desirable. However, materials having no elasticity are also usable.

As the suture needle 82, various types of known suture needles are usable. A suture needle in a straight shape, a suture needle in a curved shape, a suture needle in which only a tip end part is curved and the other part is formed in a straight shape, etc. can be selected properly.

Next, an example of usage of the above-described tissue ligating device 10 in this embodiment will be explained below with reference to FIGS. 4 to 10.

Figure 4:
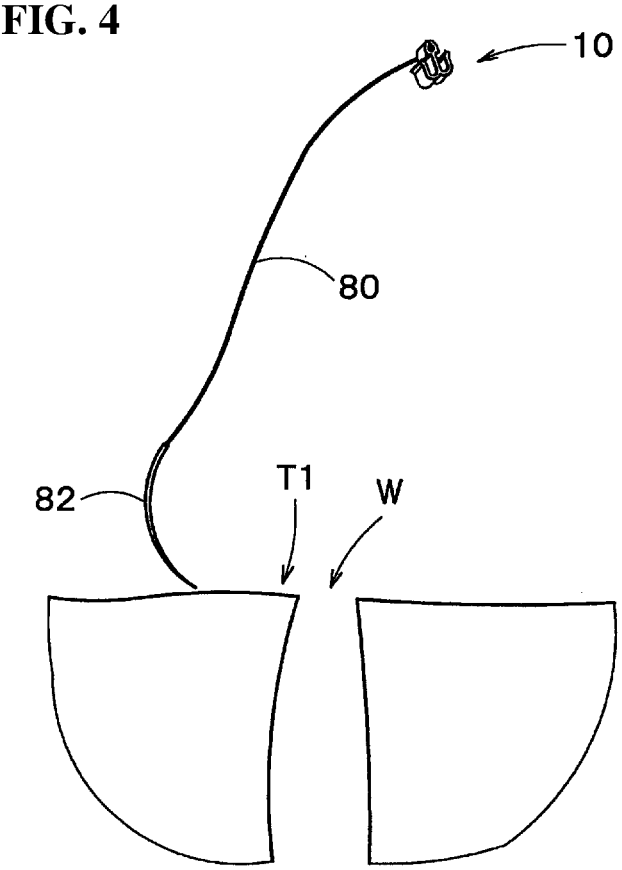
FIG. 4 is a diagram for explaining the operation of the tissue ligating device of FIG. 1 in use.
Figure 5:
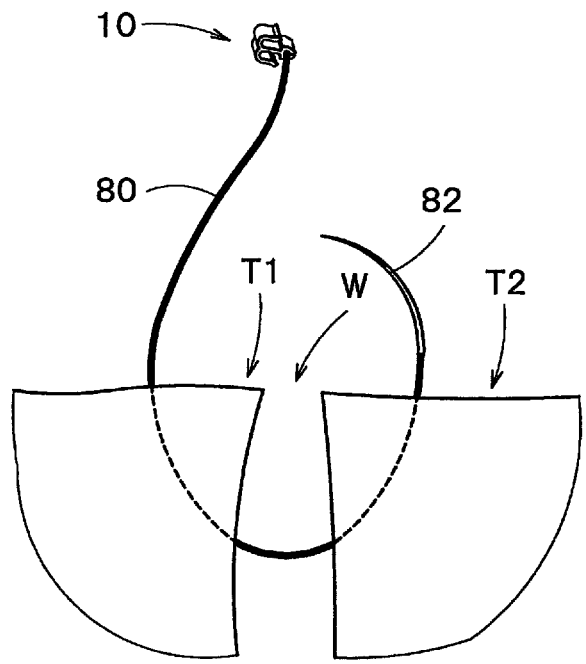
FIG. 5 is a diagram for explaining the operation of the tissue ligating device of FIG. 1 in use.

First, the suture needle 82 attached to the tip end part of the suture thread 80 is held by an operator by using a forceps or the like and then stuck into a target tissue T1 around a wound part W as shown in FIG. 4, for example. Thereafter, as shown in FIG. 5, the suture needle 80 is pulled out from a target tissue T2 opposing the target tissue T1 across the wound part W. As above, the suture thread 80 is extended through the target tissues T1 and T2 so that the wound part W can be sutured.

Figure 6:
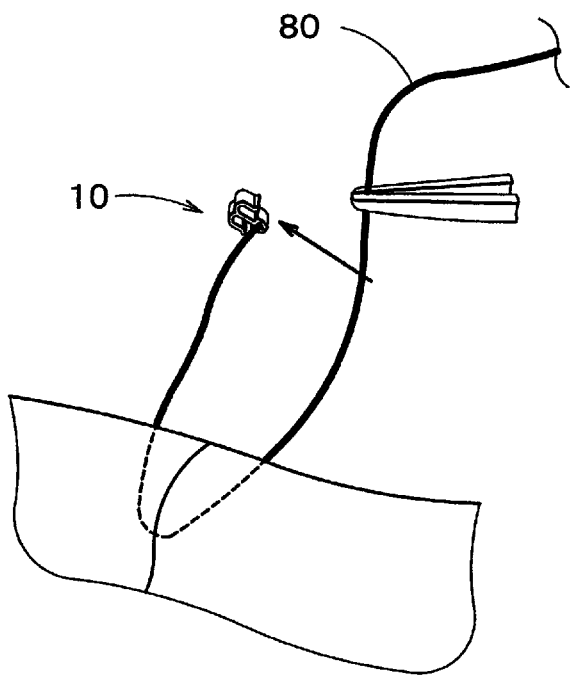
FIG. 6 is a diagram for explaining the operation of the tissue ligating device of FIG. 1 in use.

Subsequently, as shown in FIG. 6, the operator holds the suture thread 80 or the suture needle 82 with a forceps or the like and guides a part of the suture thread 80 to let it pass through a region between the back side wall part 12B and the front side wall part 12F. The part of the suture thread 80 may also be guided to pass through a region between the back side wall part 12B and the symmetrical front side wall part 13SF instead of the region between the back side wall part 12B and the front side wall part 12F.

Here, in the tissue ligating device 10 in this embodiment, the end part 12T of the front side wall part 12F far from the curved wall part 12C is inclined towards the front side. With this feature, the procedure of guiding the suture thread 80 to the region between the back side wall part 12B and the front side wall part 12F is very easy. Meanwhile, the end part of the symmetrical front side wall part 13SF far from the symmetrical curved wall part 13SC is also inclined towards the back side. With this feature, the procedure of guiding the suture thread 80 to the region between the back side wall part 12B and the symmetrical front side wall part 13SF is also very easy.

Further, as mentioned above, in the tissue ligating device 10 in this embodiment, a part of the back side wall part 12B farther from the curved wall part 12C than the end part of the front side wall part 12F far from the curved wall part 12C protrudes towards the front side to form the step part 12S. With the existence of the step part 12S, even when the suture thread 80 is going to leave the region between the back side wall part 12B and the front side wall part 12F due to its elasticity or the like, the occurrence of such leaving is advantageously prevented.

Symmetrically, as mentioned above, in the tissue ligating device 10 in this embodiment, a part of the back side wall part 12B farther from the symmetrical curved wall part 13SC than the end part of the symmetrical front side wall part 13SF far from the symmetrical curved wall part 13SC also protrudes towards the back side to form the step part 13SS. With the existence of the step part 13SS, even when the suture thread 80 is going to leave the region between the back side wall part 12B and the symmetrical front side wall part 13SF due to its elasticity or the like, the occurrence of such leaving is advantageously prevented.

Figure 7:
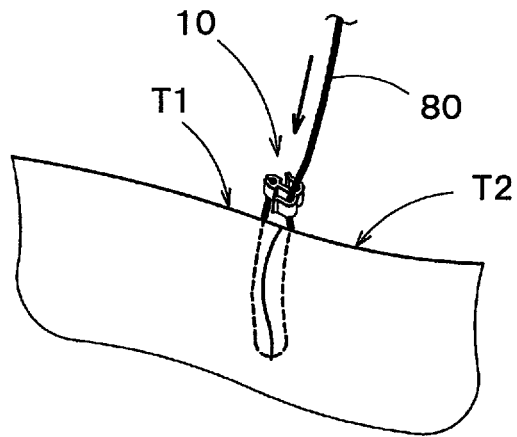
FIG. 7 is a diagram for explaining the operation of the tissue ligating device of FIG. 1 in use.

Thereafter, as shown in FIG. 7, the tip end side of the suture thread 80 is pulled away from the target tissues T1 and T2, by which the first fixation part 11 fixed to the base end part 81 of the suture thread 80 approaches the target tissue T1 and is pressed against the target tissue T1. At the same time, the suture thread 80 extending through the target tissues T1 and T2 is tightened up and the target tissues T1 and T2 are pulled together to approach each other.

Figure 8:
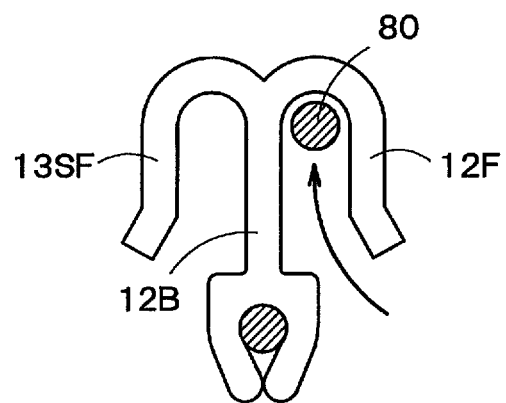
FIG. 8 is a diagram for explaining the operation of the tissue ligating device of FIG. 1 in use.
Figure 9:
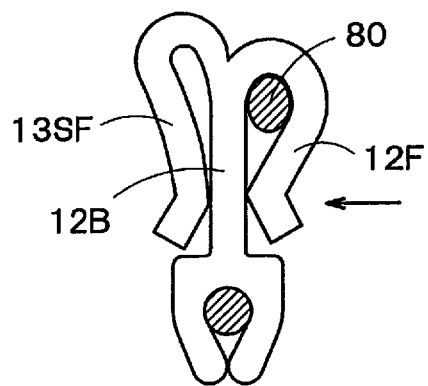
FIG. 9 is a diagram for explaining the operation of the tissue ligating device of FIG. 1 in use.

FIG. 8 shows the state of the tissue ligating device 10 at that time. As shown in FIG. 8, the suture thread 80 is extending through the region between the back side wall part 12B and the front side wall part 12F. After the suture thread 80 is tightened up sufficiently, as shown in FIG. 9, the operator crimps and deforms the symmetrical front side wall part 13SF and the front side wall part 12F with respect to the back side wall part 12B by using a forceps or the like, thereby newly fixing a part of the suture thread 80 and setting a loop starting from the base end part 81. Since the part of the front side wall part 12F other than the end part 12T and the part of the symmetrical front side wall part 13SF other than the end part 13ST are both formed in a shape like a flat plate, the procedure of crimping and deforming these parts and newly fixing a part of the suture thread 80 is very easy.

Figure 10:
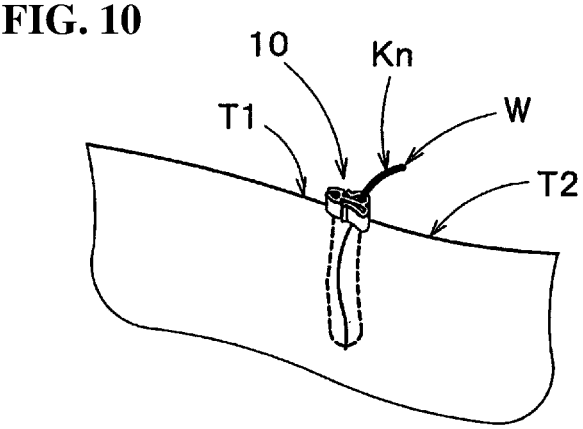
FIG. 10 is a diagram for explaining the operation of the tissue ligating device of FIG. 1 in use.

The tissue ligating device 10 in this state functions as a knot Kn of the suture thread 80. As shown in FIG. 10, the looped suture thread sutures the target tissues T1 and T2 together and closes the wound part W. The suture becomes more secure if the suturing procedure is performed while applying tension to the suture thread 80 by pulling the suture thread 80.

After the loop of the suture thread 80 starting from the base end part 81 is set, a redundant suture thread 80 is cut off by the operator. Thereafter, the removed suture thread 80 and the suture needle 82 are withdrawn to the outside of the body cavity.

As described above, according to this embodiment, the procedure of guiding the suture thread 80 to the region between the back side wall part 12B and the front side wall part 12F is very easy since the end part 12T of the front side wall part 12F far from the curved wall part 12C is inclined towards the front side. The procedure of guiding the suture thread 80 to the region between the back side wall part 12B and the symmetrical front side wall part 13SF is also very easy since the end part 13ST of the symmetrical front side wall part 13SF far from the symmetrical curved wall part 13SC is also inclined towards the back side.

Further, according to this embodiment, with the existence of the step part 12S, even when the suture thread 80 is going to leave the region between the back side wall part 12B and the front side wall part 12F due to its elasticity or the like, the occurrence of such leaving is advantageously prevented. Similarly, with the existence of the step part 13SS, even when the suture thread 80 is going to leave the region between the back side wall part 12B and the symmetrical front side wall part 13SF due to its elasticity or the like, the occurrence of such leaving is advantageously prevented.

Furthermore, according to this embodiment, postural stability of the tissue ligating device 10 is improved since the structure of the second fixation part 12 and that of the third fixation part 13 are symmetrical to each other. Operability is extremely high since both the second fixation part 12 and the third fixation part 13 are usable for the fixation of the suture thread 80.

Moreover, according to this embodiment, the part of the front side wall part 12F other than the end part 12T and the part of the symmetrical front side wall part 13SF other than the end part 13ST are both formed in a shape like a flat plate, and thus the procedure of crimping and deforming these parts and newly fixing a part of the suture thread 80 is also very easy.

Figure 11:
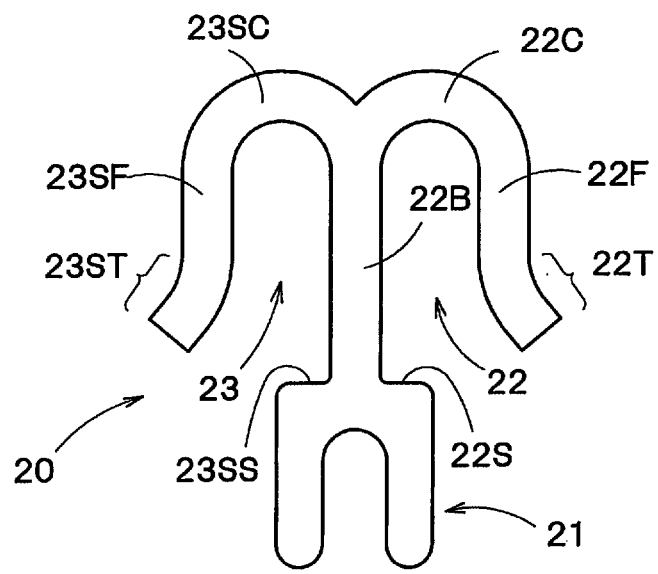
FIG. 11 is a schematic plan view showing a tissue ligating device in a second embodiment of the present invention.

Next, FIG. 11 is a schematic plan view showing a tissue ligating device in a second embodiment of the present invention.

As shown in FIG. 11, the tissue ligating device 20 in this embodiment includes a first fixation part 21 to which a base end part 81 of a suture thread 80 is fixed and a second fixation part configured to allow insertion of the suture thread 80 therethrough and allow to be crimped so as to newly fix a part of the suture thread 80, and thereby to define a loop starting from the base end part 81, in a state after ligation of tissue is performed.

The first fixation part 21 in this embodiment is configured to allow insertion of the suture thread 80 therethrough and allow to be crimped, thereby to fix a part of the suture thread 80 as the base end part 81, in a state before ligation of tissue is performed. In FIG. 11, a state before the crimping is shown.

The second fixation part 22 in this embodiment includes a back side (left-hand side in FIG. 11) wall part 22B, a front side (right-hand side in FIG. 11) wall part 22F, and a curved wall part 22C turning back from the back side wall part 22B to the front side wall part 22F like a hair pin. An end part 22T of the front side wall part 22F far from the curved wall part 22C is curved towards the front side.

Further, in the tissue ligating device 20 in this embodiment, a part of the back side wall part 22B farther from the curved wall part 22C than the end part of the front side wall part 22F far from the curved wall part 22C protrudes towards the front side to form a step part 22S.

The tissue ligating device 20 in this embodiment further includes a third fixation part 23 arranged on the other side (back side) of the second fixation part 22 symmetrically to the second fixation part 22 and configured to allow insertion of the suture thread 80 therethrough and allow to be crimped so as to newly fix a part of the suture thread 80, and thereby to define a loop starting from the base end part 81, in a state after ligation of tissue is performed.

The third fixation part 23 includes a symmetrical front side wall part 23SF that is symmetrical to the front side wall part 22F of the second fixation part with respect to the back side wall part 22B of the second fixation part and a symmetrical curved wall part 23SC turning back from the back side wall part 22B to the symmetrical front side wall part 23SF like a hair pin. An end part 23ST of the symmetrical front side wall part 23SF far from the symmetrical curved wall part 23SC is also curved towards the back side.

Further, in the tissue ligating device 20 in this embodiment, a part of the back side wall part 22B farther from the symmetrical curved wall part 23SC than the end part of the symmetrical front side wall part 23SF far from the symmetrical curved wall part 23SC protrudes towards the back side to form a step part 23SS.

A usual biocompatible stainless steel may be used as the material of the tissue ligating device 20, but not limited thereto. Laser processing is usually used as the processing method for the tissue ligating device 20, but not limited thereto, other methods such as wire electrical discharge machining may also be used.

The size of the tissue ligating device 20 is also generally as follows: the height in the vertical direction in FIG. 11 is approximately 0.8 to 1.6 mm; the width in the horizontal direction in FIG. 11 is approximately 0.3 to 1.0 mm; and the thickness in the direction orthogonal to the sheet of FIG. 11 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 20 of a relatively large size can be employed in cases of suturing a pancreatic duct (approximately φ5.0 mm) or a bile duct (approximately φ8.0 to 12.0 mm).

In this embodiment, a part of the front side wall part 22F other than the end part 22T is formed in a shape like a flat plate (thickness is approximately 0.06 to 0.10 mm). The end part 22T of the front side wall part 22F is formed in a shape like a curved surface with an arc-like cross section (thickness is also approximately 0.06 to 0.10 mm). The back side wall part 22B is formed in a shape like a flat plate (thickness is also approximately 0.06 to 0.10 mm). A part of the symmetrical front side wall part 23SF other than the end part 23ST is also formed in a shape like a flat plate (thickness is approximately 0.06 to 0.10 mm). The end part 23ST of the symmetrical front side wall part 23SF is formed in a shape like a curved surface with an arc-like cross section (thickness is also approximately 0.06 to 0.10 mm).

The length of the end part 22T of the front side wall part 22F is approximately 20% of the length of the front side wall part 22F, but is not limited thereto. As for the proportion between sizes, the length of the end part 22T of the front side wall part 22F is desired to be 10 to 40% of the length of the front side wall part 22F. In this embodiment, the end part 22T of the front side wall part 22F smoothly continues from the part of the front side wall part 22F other than the end part 22T to have a surface on the front side as a curved surface with a curvature radius of 0.14 mm, but is not limited thereto. The curvature radius of the end part 22T's surface on the front side (outer side) can be selected from a wide range of 0.05 to 2.0 mm or a preferable range of 0.10 to 1.0 mm.

Symmetrically, the length of the end part 22ST of the symmetrical front side wall part 23SF is approximately 20% of the length of the symmetrical front side wall part 23SF, but is not limited thereto. As for the proportion between sizes, the length of the end part 23ST of the symmetrical front side wall part 23SF is desired to be 10 to 40% of the length of the symmetrical front side wall part 23SF. In this embodiment, the end part 23ST of the symmetrical front side wall part 23SF smoothly continues from the part of the symmetrical front side wall part 23SF other than the end part 23ST to have a surface on the back side as a curved surface with a curvature radius of 0.14 mm, but is not limited thereto. The curvature radius of the end part 23ST's surface on the back side (outer side) can be selected from a wide range of 0.05 to 2.0 mm or a preferable range of 0.10 to 1.0 mm.

The above-described tissue ligating device 20 of the second embodiment can also be used according to a method of usage similar to the method explained referring to FIGS. 4 to 10.

Here, in the tissue ligating device 20 in this embodiment, the end part 22T of the front side wall part 22F far from the curved wall part 22C is curved towards the front side. With this feature, the procedure of guiding the suture thread 80 to the region between the back side wall part 22B and the front side wall part 22F is very easy. Meanwhile, the end part of the symmetrical front side wall part 23SF far from the symmetrical curved wall part 23SC is also curved towards the back side. With this feature, the procedure of guiding the suture thread 80 to the region between the back side wall part 22B and the symmetrical front side wall part 23SF is also very easy.

Further, according to this embodiment, with the existence of the step part 22S, even when the suture thread 80 is going to leave the region between the back side wall part 22B and the front side wall part 22F due to its elasticity or the like, the occurrence of such leaving is advantageously prevented.

Similarly, with the existence of the step part 23SS, even when the suture thread 80 is going to leave the region between the back side wall part 22B and the symmetrical front side wall part 23SF due to its elasticity or the like, the occurrence of such leaving is advantageously prevented.

Furthermore, according to this embodiment, postural stability of the tissue ligating device 20 is improved since the structure of the second fixation part 22 and that of the third fixation part 23 are symmetrical to each other. Operability is extremely high since both the second fixation part 22 and the third fixation part 23 are usable for the fixation of the suture thread 80.

Moreover, according to this embodiment, the part of the front side wall part 22F other than the end part 22T and the part of the symmetrical front side wall part 23SF other than the end part 23ST are both formed in a shape like a flat plate, and thus the procedure of crimping and deforming these parts and newly fixing a part of the suture thread 80 is also very easy.

Figure 12:
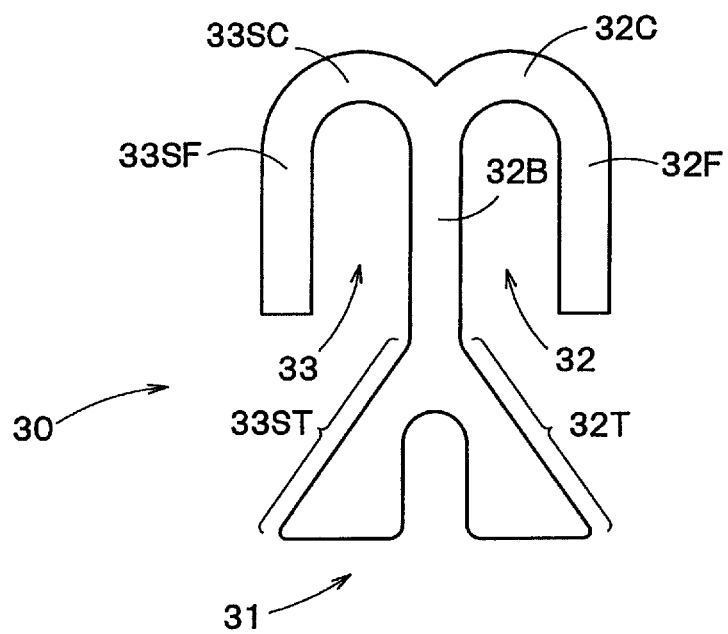
FIG. 12 is a schematic plan view showing a tissue ligating device in a third embodiment of the present invention.

Next, FIG. 12 is a schematic plan view showing a tissue ligating device in a third embodiment of the present invention.

As shown in FIG. 12, the tissue ligating device 30 in this embodiment includes a first fixation part 31 to which a base end part 81 of a suture thread 80 is fixed and a second fixation part configured to allow insertion of the suture thread 80 therethrough and allow to be crimped so as to newly fix a part of the suture thread 80, and thereby to define a loop starting from the base end part 81, in a state after ligation of tissue is performed.

The first fixation part 31 in this embodiment is configured to allow insertion of the suture thread 80 therethrough and allow to be crimped, thereby to fix a part of the suture thread 80 as the base end part 81, in a state before ligation of tissue is performed. In FIG. 12, a state before the crimping is shown.

The second fixation part 32 in this embodiment includes a back side (left-hand side in FIG. 12) wall part 32B, a front side (right-hand side in FIG. 12) wall part 32F, and a curved wall part 32C turning back from the back side wall part 32B to the front side wall part 32F like a hair pin. The back side wall part 32B is longer than the front side wall part 32F, and a part of the back side wall part 32B farther from the curved wall part 32C than the end part of the front side wall part 32F far from the curved wall part 32C has a surface 32T inclined towards the front side (The surface 32T is explained as a part of the back side wall part 32B of "the second fixation part 32 configured to allow insertion of the suture thread 80 therethrough and allow to be crimped so as to newly fix a part of the suture thread 80, and thereby to define a loop starting from the base end part 81", because the surface 32T is not involved in the "fixation" of the suture thread 80 but is involved in the "insertion" of the suture thread 80 before the fixation.).

The tissue ligating device 30 in this embodiment further includes a third fixation part 33 arranged on the other side (back side) of the third fixation part 32 symmetrically to the second fixation part 32 and configured to allow insertion of the suture thread 80 therethrough and allow to be crimped so as to newly fix a part of the suture thread 80, and thereby to define a loop starting from the base end part 81, in a state after ligation of tissue is performed.

The third fixation part 33 includes a symmetrical front side wall part 33SF that is symmetrical to the front side wall part 32F of the second fixation part with respect to the back side wall part 32B of the second fixation part and a symmetrical curved wall part 33SC turning back from the back side wall part 32B to the symmetrical front side wall part 33SF like a hair pin. The back side wall part 32B is longer than the symmetrical front side wall part 32SF, and a part of the back side wall part 32B farther from the symmetrical curved wall part 32SC than the end part of the symmetrical front side wall part 32SF far from the symmetrical curved wall part 32SC also has a surface 33ST inclined towards the back side (The surface 33ST is also explained as a part of the back side wall part 32B of "the third fixation part 33 configured to allow insertion of the suture thread 80 therethrough and allow to be crimped so as to newly fix a part of the suture thread 80, and thereby to define a loop starting from the base end part 81", because the surface 33ST is not involved in the "fixation" of the suture thread 80 but is involved in the "insertion" of the suture thread 80 before the fixation.).

A usual biocompatible stainless steel may be used as the material of the tissue ligating device 30, but not limited thereto. Laser processing is usually used as the processing method for the tissue ligating device 30, but not limited thereto, other methods such as wire electrical discharge machining may also be used.

The size of the tissue ligating device 30 is also generally as follows: the height in the vertical direction in FIG. 12 is approximately 0.8 to 1.6 mm; the width in the horizontal direction in FIG. 12 is approximately 0.3 to 1.0 mm; and the thickness in the direction orthogonal to the sheet of FIG. 12 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 30 of a relatively large size can be employed in cases of suturing a pancreatic duct (approximately φ5.0 mm) or a bile duct (approximately φ8.0 to 12.0 mm).

In this embodiment, the front side wall part 32F and the symmetrical front side wall part 33SF are both formed in a shape like a flat plate (thickness is approximately 0.06 to 0.10 mm). A part of the back side wall part 32B closer to the curved wall part 32C than the inclined surfaces 32T and 33ST is also formed in a shape like a flat plate (thickness is also approximately 0.06 to 0.10 mm). In this embodiment, the symmetrical inclined surfaces 32T and 33ST of the back side wall part 32B are both inclined at an angle of 40 degrees with respect to the flat plate-shaped part of the back side wall part 32B, but is not limited thereto. The inclination angle can be selected from a wide range of 10 to 80 degrees or a preferable range of 20 to 60 degrees.

The above-described tissue ligating device 30 of the third embodiment can also be used according to a method of usage similar to the method explained referring to FIGS. 4 to 10.

Here, in the tissue ligating device 30 in this embodiment, a part of the back side wall part 32B farther from the curved wall part 32C than the end part of the front side wall part 32F far from the curved wall part 32C has the surface 32T inclined towards the front side. With this feature, the procedure of guiding the suture thread 80 to the region between the back side wall part 32B and the front side wall part 32F is very easy. Meanwhile, a part of the back side wall part 32B farther from the symmetrical curved wall part 32SC than the end part of the symmetrical front side wall part 32SF far from the symmetrical curved wall part 32SC has the surface 33ST inclined towards the back side. With this feature, the procedure of guiding the suture thread 80 to the region between the back side wall part 32B and the symmetrical front side wall part 33SF is also very easy.

Furthermore, according to this embodiment, postural stability of the tissue ligating device 30 is improved since the structure of the second fixation part 32 and that of the third fixation part 33 are symmetrical to each other. Operability is extremely high since both the second fixation part 32 and the third fixation part 33 are usable for the fixation of the suture thread 80.

Figure 13:
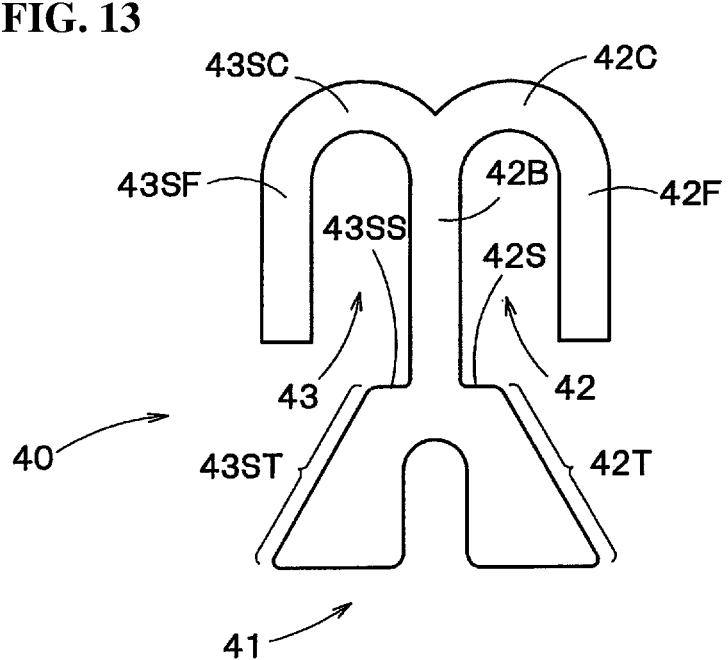
FIG. 13 is a schematic plan view showing a tissue ligating device in a fourth embodiment of the present invention.

Next, FIG. 13 is a schematic plan view showing a tissue ligating device in a fourth embodiment of the present invention.

As shown in FIG. 13, the tissue ligating device 40 in this embodiment includes a first fixation part 41 to which a base end part 81 of a suture thread 80 is fixed and a second fixation part 42 configured to allow insertion of the suture thread 80 therethrough and allow to be crimped so as to newly fix a part of the suture thread 80, and thereby to define a loop starting from the base end part 81, in a state after ligation of tissue is performed.

The first fixation part 41 in this embodiment is configured to allow insertion of the suture thread 80 therethrough and allow to be crimped, thereby to fix a part of the suture thread 80 as the base end part 81, in a state before ligation of tissue is performed. In FIG. 13, a state before the crimping is shown.

The second fixation part 42 in this embodiment includes a back side (left-hand side in FIG. 13) wall part 42B, a front side (right-hand side in FIG. 13) wall part 42F, and a curved wall part 42C turning back from the back side wall part 42B to the front side wall part 42F like a hair pin. The back side wall part 42B is longer than the front side wall part 42F, and a part of the back side wall part 42B farther from the curved wall part 42C than the end part of the front side wall part 42F far from the curved wall part 42C has a surface 42S rising towards the front side and a surface 42T continuing to the rising surface 42S and inclined towards the front side (The surface 42T is explained as a part of the back side wall part 42B of "the second fixation part 42 configured to allow insertion of the suture thread 80 therethrough and allow to be crimped so as to newly fix a part of the suture thread 80, and thereby to define a loop starting from the base end part 81", because the surface 42T is not involved in the "fixation" of the suture thread 80 but is involved in the "insertion" of the suture thread 80 before the fixation.).

The tissue ligating device 40 in this embodiment further includes a third fixation part 43 arranged on the other side (back side) of the third fixation part 42 symmetrically to the second fixation part 42 and configured to allow insertion of the suture thread 80 therethrough and allow to be crimped so as to newly fix a part of the suture thread 80, and thereby to define a loop starting from the base end part 81, in a state after ligation of tissue is performed.

The third fixation part 43 includes a symmetrical front side wall part 43SF that is symmetrical to the front side wall part 42F of the second fixation part with respect to the back side wall part 42B of the second fixation part and a symmetrical curved wall part 43SC turning back from the back side wall part 42B to the symmetrical front side wall part 43SF like a hair pin. The back side wall part 42B is longer than the symmetrical front side wall part 42SF, and a part of the back side wall part 42B farther from the symmetrical curved wall part 42SC than the end part of the symmetrical front side wall part 42SF far from the symmetrical curved wall part 42SC also has a surface 43SS rising towards the back side and a surface 43ST connected to the rising surface 43SS and inclined towards the back side (The surface 43ST is also explained as a part of the back side wall part 42B of "the third fixation part 43 configured to allow insertion of the suture thread 80 therethrough and allow to be crimped so as to newly fix a part of the suture thread 80, and thereby to define a loop starting from the base end part 81", because the surface 43ST is not involved in the "fixation" of the suture thread 80 but is involved in the "insertion" of the suture thread 80 before the fixation.).

A usual biocompatible stainless steel may be used as the material of the tissue ligating device 40, but not limited thereto. Laser processing is usually used as the processing method for the tissue ligating device 40, but not limited thereto, other methods such as wire electrical discharge machining may also be used.

The size of the tissue ligating device 40 is also generally as follows: the height in the vertical direction in FIG. 13 is approximately 0.8 to 1.6 mm; the width in the horizontal direction in FIG. 13 is approximately 0.3 to 1.0 mm; and the thickness in the direction orthogonal to the sheet of FIG. 13 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 30 of a relatively large size can be employed in cases of suturing a pancreatic duct (approximately φ5.0 mm) or a bile duct (approximately φ8.0 to 12.0 mm).

In this embodiment, the front side wall part 42F and the symmetrical front side wall part 43SF are formed in a shape like a flat plate (thickness is approximately 0.06 to 0.10 mm). A part of the back side wall part 42B closer to the curved wall part 42C than the rising surfaces 42S and 43SS is also formed in a shape like a flat plate (thickness is also approximately 0.06 to 0.10 mm). In this embodiment, the symmetrical inclined surfaces 42T and 43ST of the back side wall part 32B are both inclined at an angle of 40 degrees with respect to the flat plate-shaped part of the back side wall part 42B, but is not limited thereto. The inclination angle can be selected from a wide range of 10 to 80 degrees or a preferable range of 20 to 60 degrees.

The above-described tissue ligating device 40 of the fourth embodiment can also be used according to a method of usage similar to the method explained referring to FIGS. 4 to 10.

Here, in the tissue ligating device 40 in this embodiment, a part of the back side wall part 42B farther from the curved wall part 42C than the end part of the front side wall part 42F far from the curved wall part 42C has the surface 42T inclined towards the front side. With this feature, the procedure of guiding the suture thread 80 to the region between the back side wall part 42B and the front side wall part 42F is very easy. Meanwhile, a part of the back side wall part 42B farther from the symmetrical curved wall part 42SC than the end part of the symmetrical front side wall part 42SF far from the symmetrical curved wall part 42SC has the surface 43ST inclined towards the back side. With this feature, the procedure of guiding the suture thread 80 to the region between the back side wall part 42B and the symmetrical front side wall part 43SF is also very easy.

Further, according to this embodiment, with the existence of the rising surfaces 42S and 43SS, even when the suture thread 80 is going to leave the region between the back side wall part 42B and the front side wall part 42F or the region between the back side wall part 42B and the symmetrical front side wall part 43SF due to its elasticity or the like, the occurrence of such leaving is advantageously prevented.

Furthermore, according to this embodiment, postural stability of the tissue ligating device 40 is improved since the structure of the second fixation part 42 and that of the third fixation part 43 are symmetrical to each other. Operability is extremely high since both the second fixation part 42 and the third fixation part 43 are usable for the fixation of the suture thread 80.

Figure 14:
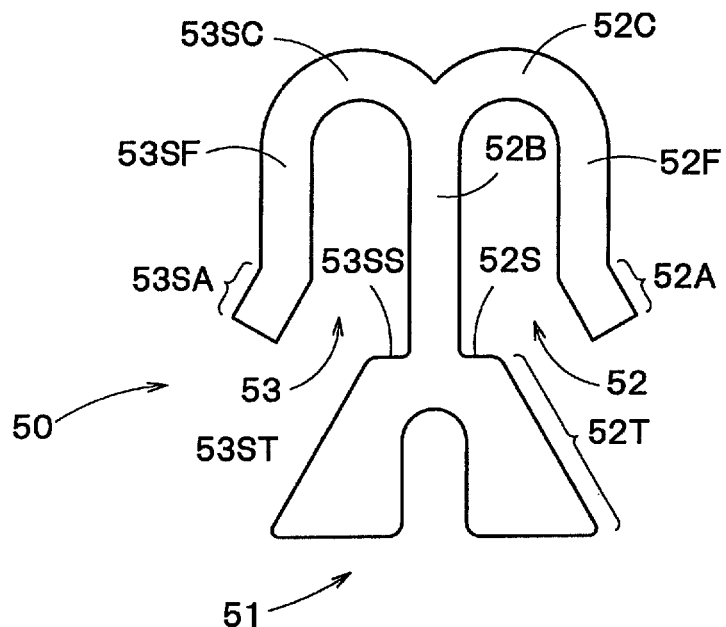
FIG. 14 is a schematic plan view showing a tissue ligating device in a fifth embodiment of the present invention.

Next, FIG. 14 is a schematic plan view showing a tissue ligating device in a fifth embodiment of the present invention.

As shown in FIG. 14, the tissue ligating device 50 in this embodiment includes a first fixation part 51 to which a base end part 81 of a suture thread 80 is fixed, and a second fixation part configured to allow insertion of the suture thread 80 therethrough and allow to be crimped so as to newly fix a part of the suture thread 80, thereby to define a loop starting from the base end part 81, in a state after ligation of tissue is performed.

The first fixation part 51 in this embodiment is configured to allow insertion of the suture thread 80 therethrough and allow to be crimped, thereby to fix a part of the suture thread 80 as the base end part 81, in a state before ligation of tissue is performed. In FIG. 14, a state before the crimping is shown.

The second fixation part 52 in this embodiment includes a back side (left-hand side in FIG. 14) wall part 52B, a front side (right-hand side in FIG. 14) wall part 52F, and a curved wall part 52C turning back from the back side wall part 52B to the front side wall part 52F like a hair pin. An end part 52A of the front side wall part 52F far from the curved wall part 52C is inclined towards the front side. The back side wall part 52B is longer than the front side wall part 52F, and a part of the back side wall part 52B farther from the curved wall part 52C than the end part of the front side wall part 52F far from the curved wall part 52C has a surface 52S rising towards the front side and a surface 52T continuing to the rising surface 52S and inclined towards the front side (The surface 52T is explained as a part of the back side wall part 52B of "the second fixation part 52 configured to allow insertion of the suture thread 80 therethrough and allow to be crimped so as to newly fix a part of the suture thread 80, thereby to define a loop starting from the base end part 81", because the surface 52T is not involved in the "fixation" of the suture thread 80 but is involved in the "insertion" of the suture thread 80 before the fixation.).

The tissue ligating device 50 in this embodiment further includes a third fixation part 53 arranged on the other side (back side) of the third fixation part 52 symmetrically to the second fixation part 52 and configured to allow insertion of the suture thread 80 therethrough and allow to be crimped so as to newly fix a part of the suture thread 80, thereby to define a loop starting from the base end part 81, in a state after ligation of tissue is performed.

The third fixation part 53 includes a symmetrical front side wall part 53SF that is symmetrical to the front side wall part 52F of the second fixation part with respect to the back side wall part 52B of the second fixation part and a symmetrical curved wall part 53SC turning back from the back side wall part 52B to the symmetrical front side wall part 53SF like a hair pin. An end part 53SA of the symmetrical front side wall part 53SF far from the symmetrical curved wall part 53SC is also inclined towards the back side. The back side wall part 52B is longer than the symmetrical front side wall part 52SF, and a part of the back side wall part 52B farther from the symmetrical curved wall part 52SC than the end part of the symmetrical front side wall part 52SF far from the symmetrical curved wall part 52SC also has a surface 53SS rising towards the back side and a surface 53ST continuing to the rising surface 53SS and inclined towards the back side (The surface 53ST is also explained as a part of the back side wall part 52B of "the third fixation part 53 configured to allow insertion of the suture thread 80 therethrough and allow to be crimped so as to newly fix a part of the suture thread 80, thereby to define a loop starting from the base end part 81", because the surface 53ST is not involved in the "fixation" of the suture thread 80 but is involved in the "insertion" of the suture thread 80 before the fixation.).

A usual biocompatible stainless steel may be used as the material of the tissue ligating device 50, but not limited thereto. Laser processing is usually used as the processing method for the tissue ligating device 50, but not limited thereto, other methods such as wire electrical discharge machining may also be used.

The size of the tissue ligating device 50 is also generally as follows: the height in the vertical direction in FIG. 14 is approximately 0.8 to 1.6 mm; the width in the horizontal direction in FIG. 14 is approximately 0.3 to 1.0 mm; and the thickness in the direction orthogonal to the sheet of FIG. 14 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 30 of a relatively large size can be employed in cases of suturing a pancreatic duct (approximately φ5.0 mm) or a bile duct (approximately φ8.0 to 12.0 mm).

In this embodiment, a part of the front side wall part 52F other than the end part 52A is formed in a shape like a flat plate (thickness is approximately 0.06 to 0.10 mm). The end part 52A of the front side wall part 52F is also formed in a shape like a flat plate (thickness is also approximately 0.06 to 0.10 mm). A part of the symmetrical front side wall part 53SF other than the end part 53SA is also formed in a shape like a flat plate (thickness is approximately 0.06 to 0.10 mm). The end part 53SA of the symmetrical front side wall part 53SF is also formed in a shape like a flat plate (thickness is also approximately 0.06 to 0.10 mm). A part of the back side wall part 52B closer to the curved wall part 52C than the rising surfaces 52S and 53SS is also formed in a shape like a flat plate (thickness is also approximately 0.06 to 0.10 mm). In this embodiment, the symmetrical inclined surfaces 52T and 53ST of the back side wall part 52B are both inclined at an angle of 40 degrees with respect to the flat plate-shaped part of the back side wall part 52B, but is not limited thereto. The inclination angle can be selected from a wide range of 10 to 80 degrees or a preferable range of 20 to 60 degrees.

The length of the end part 52A of the front side wall part 52F is approximately 20% of the length of the front side wall part 52F, but is not limited thereto. As for the proportion between sizes, the length of the end part 52A of the front side wall part 52F is desired to be 10 to 40% of the length of the front side wall part 52F. In this embodiment, the end part 52A of the front side wall part 52F is inclined by 30 degrees with respect to the part of the front side wall part 52F other than the end part 52A, but is not limited thereto. The inclination angle can be selected from a wide range of 10 to 80 degrees or a preferable range of 20 to 60 degrees.

Symmetrically, the length of the end part 53SA of the symmetrical front side wall part 53SF is approximately 20% of the length of the symmetrical front side wall part 53SF, but is not limited thereto. As for the proportion between sizes, the length of the end part 53SA of the symmetrical front side wall part 53SF is desired to be 10 to 40% of the length of the symmetrical front side wall part 53SF. In this embodiment, the end part 53SA of the symmetrical front side wall part 53SF is inclined by 30 degrees with respect to the part of the symmetrical front side wall part 53SF other than the end part 53SA, but is not limited thereto. The inclination angle can be selected from a wide range of 10 to 80 degrees or a preferable range of 20 to 60 degrees.

The above-described tissue ligating device 50 of the fifth embodiment can also be used according to a method of usage similar to the method explained referring to FIGS. 4 to 10.

Here, in the tissue ligating device 50 in this embodiment, a part of the back side wall part 52B farther from the curved wall part 52C than the end part of the front side wall part 52F far from the curved wall part 52C has the surface 52T inclined towards the front side. The end part 52A of the front side wall part 52F far from the curved wall part 52C is inclined towards the front side. With these features, the procedure of guiding the suture thread 80 to the region between the back side wall part 52B and the front side wall part 52F is very easy.

A part of the back side wall part 52B farther from the symmetrical curved wall part 52SC than the end part of the symmetrical front side wall part 52SF far from the symmetrical curved wall part 52SC has the surface 53ST inclined towards the back side. The end part 53SA of the symmetrical front side wall part 53SF far from the symmetrical curved wall part 53SC is also inclined towards the back side. With these features, the procedure of guiding the suture thread 80 to the region between the back side wall part 52B and the symmetrical front side wall part 53SF is also very easy.

Further, according to this embodiment, with the existence of the rising surfaces 52S and 53SS, even when the suture thread 80 is going to leave the region between the back side wall part 52B and the front side wall part 52F or the region between the back side wall part 52B and the symmetrical front side wall part 53SF due to its elasticity or the like, the occurrence of such leaving is advantageously prevented.

Furthermore, according to this embodiment, postural stability of the tissue ligating device 50 is improved since the structure of the second fixation part 52 and that of the third fixation part 53 are symmetrical to each other. Operability is extremely high since both the second fixation part 52 and the third fixation part 53 are usable for the fixation of the suture thread 80.

Moreover, according to this embodiment, the part of the front side wall part 52F other than the end part 52A and the part of the symmetrical front side wall part 53SF other than the end part 53SA are both formed in a shape like a flat plate, and thus the procedure of crimping and deforming these parts and newly fixing a part of the suture thread 80 is also very easy.

Figure 15:
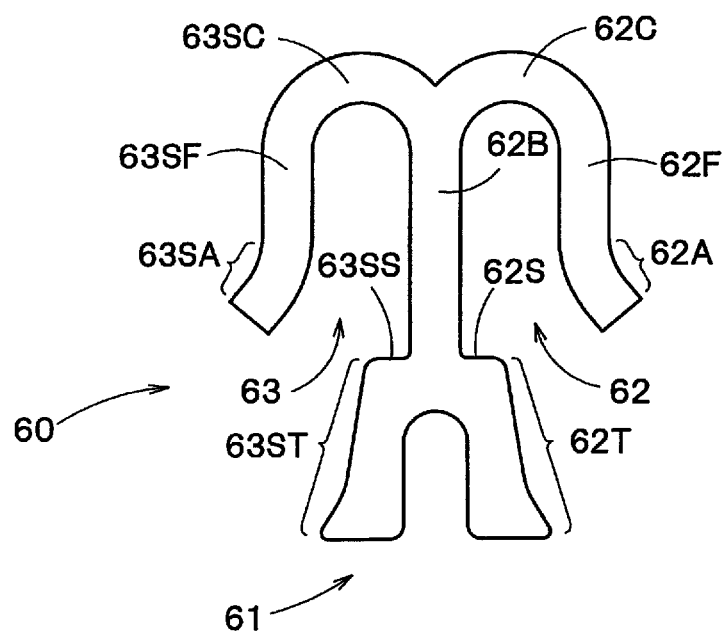
FIG. 15 is a schematic plan view showing a tissue ligating device in a sixth embodiment of the present invention.
Figure 16:
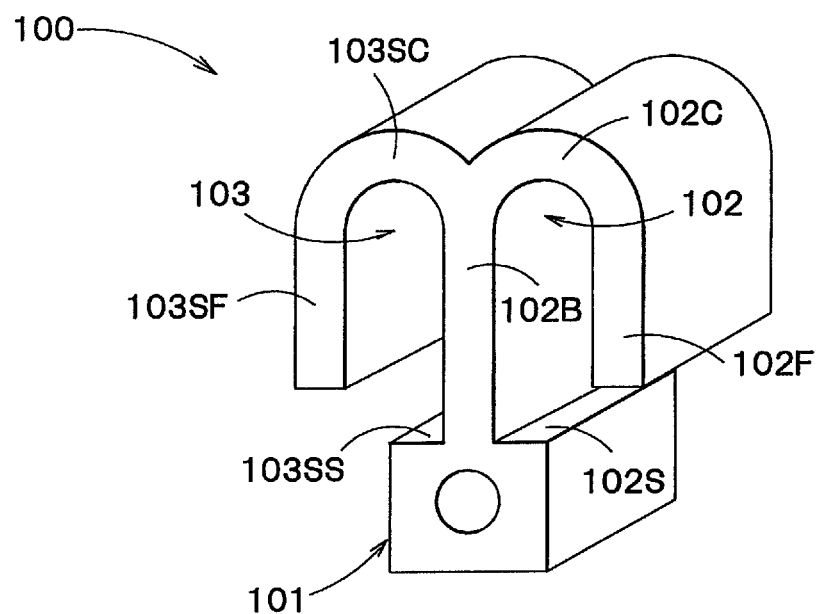
FIG. 16 is a schematic perspective view showing a tissue ligating device disclosed in JP2012130669A.
Figure 17:
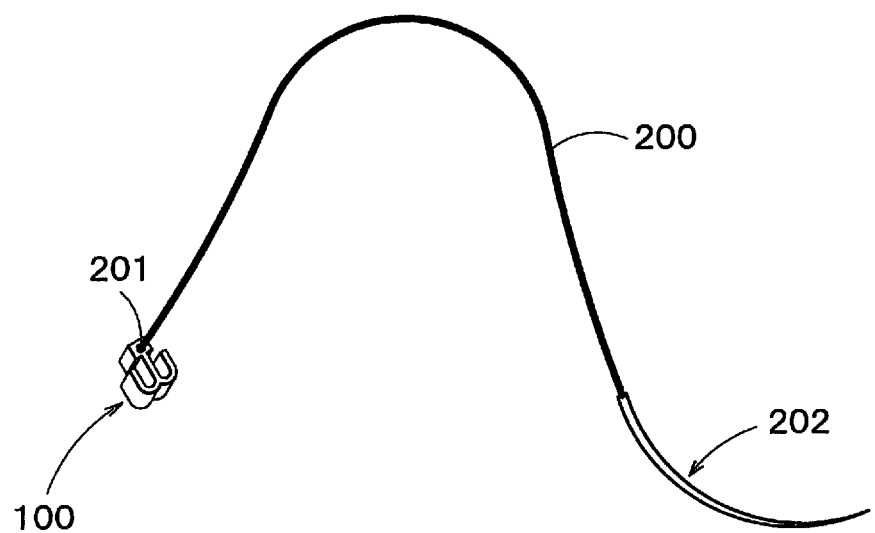
FIG. 17 is a schematic perspective view showing a state in which a suture thread has been fixed to a first fixation part of the tissue ligating device of FIG. 16.
Figure 18:
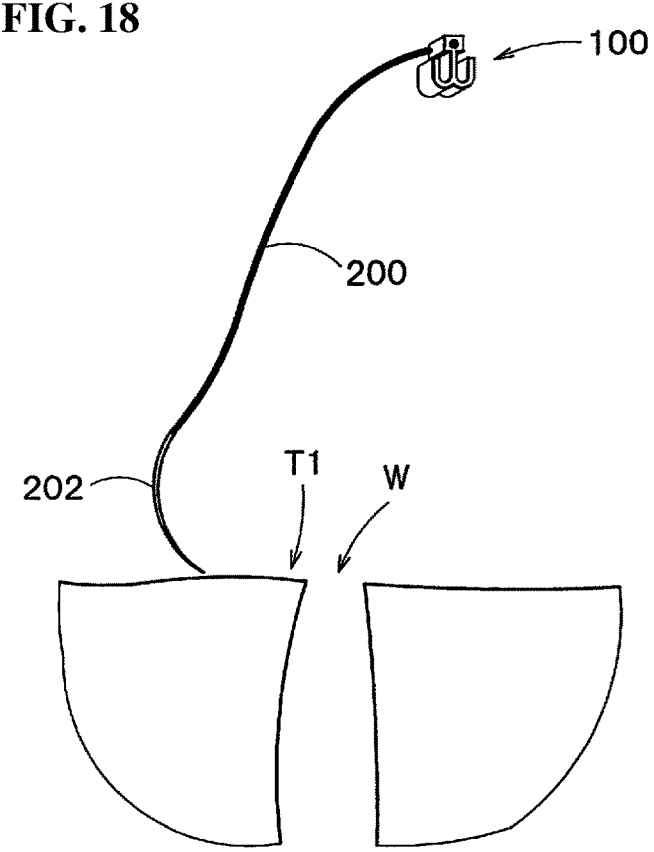
FIG. 18 is a diagram for explaining the operation of the tissue ligating device of FIG. 16 in use.
Figure 19:
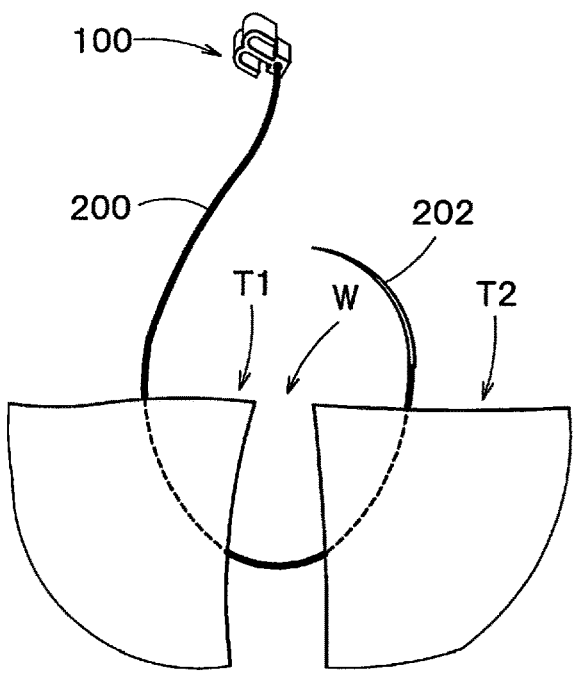
FIG. 19 is a diagram for explaining the operation of the tissue ligating device of FIG. 16 in use.
Figure 20:
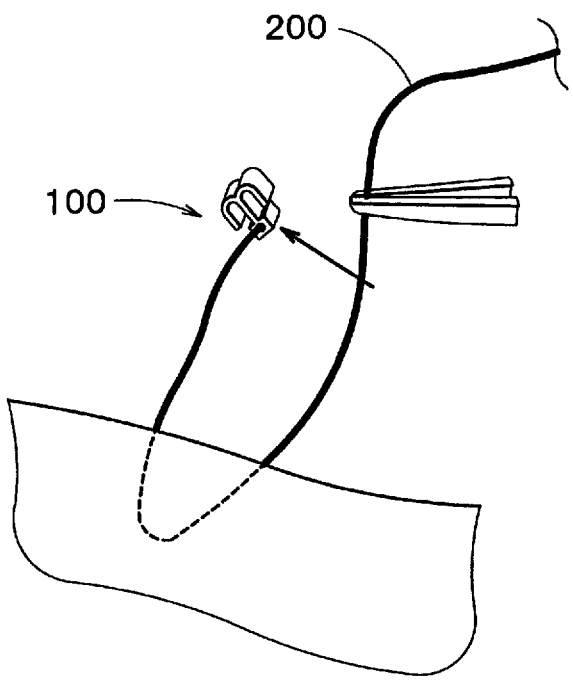
FIG. 20 is a diagram for explaining the operation of the tissue ligating device of FIG. 16 in use.
Figure 21:
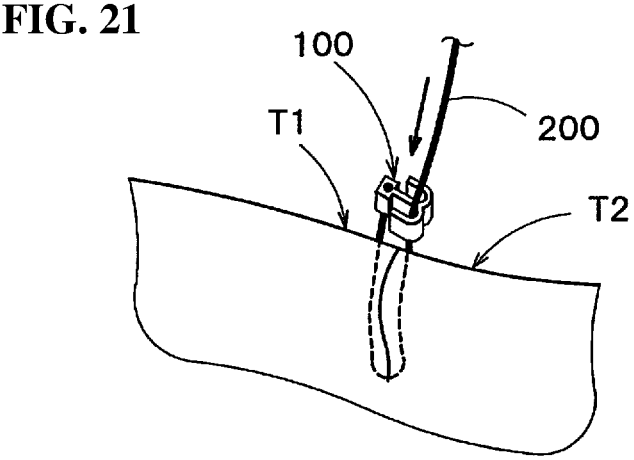
FIG. 21 is a diagram for explaining the operation of the tissue ligating device of FIG. 16 in use.
Figure 22:
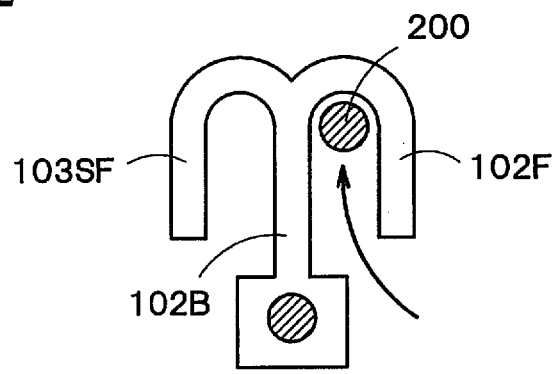
FIG. 22 is a diagram for explaining the operation of the tissue ligating device of FIG. 16 in use.
Figure 23:
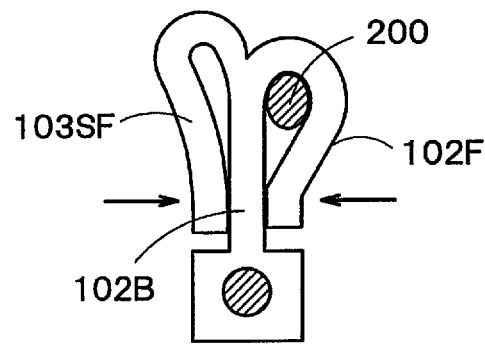
FIG. 23 is a diagram for explaining the operation of the tissue ligating device of FIG. 16 in use.
Figure 24:
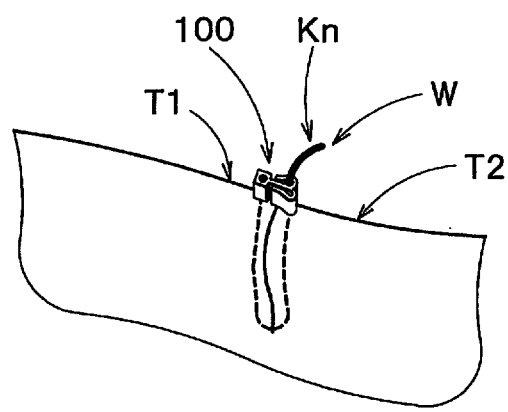
FIG. 24 is a diagram for explaining the operation of the tissue ligating device of FIG. 16 in use.

Next, FIG. 15 is a schematic plan view showing a tissue ligating device in a sixth embodiment of the present invention.

As shown in FIG. 15, the tissue ligating device 60 in this embodiment includes a first fixation part 61 to which a base end part 81 of a suture thread 80 is fixed and a second fixation part configured to allow insertion of the suture thread 80 therethrough and allow to be crimped so as to newly fix a part of the suture thread 80, and thereby to define a loop starting from the base end part 81, in a state after ligation of tissue is performed.

The first fixation part 61 in this embodiment is configured to allow insertion of the suture thread 80 therethrough and allow to be crimped, thereby to fix a part of the suture thread 80 as the base end part 81, in a state before ligation of tissue is performed. In FIG. 15, a state before the crimping is shown.

The second fixation part 62 in this embodiment includes a back side (left-hand side in FIG. 15) wall part 62B, a front side (right-hand side in FIG. 15) wall part 62F, and a curved wall part 62C turning back from the back side wall part 62B to the front side wall part 62F like a hair pin. An end part 62A of the front side wall part 62F far from the curved wall part 62C is curved towards the front side. The back side wall part 62B is longer than the front side wall part 62F, and a part of the back side wall part 62B farther from the curved wall part 62C than the end part of the front side wall part 62F far from the curved wall part 62C has a surface 62S rising towards the front side and a surface 62T continuing to the rising surface 62S and inclined towards the front side (The surface 62T is explained as a part of the back side wall part 62B of "the second fixation part 62 configured to allow insertion of the suture thread 80 therethrough and allow to be crimped so as to newly fix a part of the suture thread 80, and thereby to define a loop starting from the base end part 81", because the surface 62T is not involved in the "fixation" of the suture thread 80 but is involved in the "insertion" of the suture thread 80 before the fixation.).

The tissue ligating device 60 in this embodiment further includes a third fixation part 63 arranged on the other side (back side) of the third fixation part 62 symmetrically to the second fixation part 62 and configured to allow insertion of the suture thread 80 therethrough and allow to be crimped so as to newly fix a part of the suture thread 80, and thereby to define a loop starting from the base end part 81, in a state after ligation of tissue is performed.

The third fixation part 63 includes a symmetrical front side wall part 63SF that is symmetrical to the front side wall part 62F of the second fixation part with respect to the back side wall part 62B of the second fixation part and a symmetrical curved wall part 63SC turning back from the back side wall part 62B to the symmetrical front side wall part 63SF like a hair pin. An end part 63SA of the symmetrical front side wall part 63SF far from the symmetrical curved wall part 63SC is also curved towards the back side. The back side wall part 62B is longer than the symmetrical front side wall part 62SF, and a part of the back side wall part 62B farther from the symmetrical curved wall part 62SC than the end part of the symmetrical front side wall part 62SF far from the symmetrical curved wall part 62SC also has a surface 63SS rising towards the back side and a surface 63ST continuing to the rising surface 63SS and inclined towards the back side (The surface 63ST is also explained as a part of the back side wall part 62B of "the third fixation part 63 configured to allow insertion of the suture thread 80 therethrough and allow to be crimped so as to newly fix a part of the suture thread 80, and thereby to define a loop starting from the base end part 81", because the surface 63ST is not involved in the "fixation" of the suture thread 80 but is involved in the "insertion" of the suture thread 80 before the fixation.).

A usual biocompatible stainless steel may be used as the material of the tissue ligating device 60, but not limited thereto. Laser processing is usually used as the processing method for the tissue ligating device 60, but not limited thereto, other methods such as wire electrical discharge machining may also be used.

The size of the tissue ligating device 60 is also generally as follows: the height in the vertical direction in FIG. 15 is approximately 0.8 to 1.6 mm; the width in the horizontal direction in FIG. 15 is approximately 0.3 to 1.0 mm; and the thickness in the direction orthogonal to the sheet of FIG. 15 is approximately 0.5 to 1.3 mm. While a tissue ligating device 10 of a relatively small size is employed in cases of suturing a blood vessel of a relatively small diameter (approximately φ1.5 to 2.0 mm), a tissue ligating device 30 of a relatively large size can be employed in cases of suturing a pancreatic duct (approximately φ5.0 mm) or a bile duct (approximately φ8.0 to 12.0 mm).

In this embodiment, a part of the front side wall part 62F other than the end part 62A is formed in a shape like a flat plate (thickness is approximately 0.06 to 0.10 mm). The end part 62A of the front side wall part 62F is formed in a shape like a curved surface with an arc-like cross section (thickness is also approximately 0.06 to 0.10 mm). A part of the back side wall part 62B closer to the curved wall part 62C than the rising surfaces 62S and 63SS is also formed in a shape like a flat plate (thickness is also approximately 0.06 to 0.10 mm). A part of the symmetrical front side wall part 63SF other than the end part 63SA is also formed in a shape like a flat plate (thickness is approximately 0.06 to 0.10 mm). The end part 63SA of the symmetrical front side wall part 63SF is formed in a shape like a curved surface with an arc-like cross section (thickness is also approximately 0.06 to 0.10 mm).

The length of the end part 62A of the front side wall part 62F is approximately 20% of the length of the front side wall part 62F, but is not limited thereto. As for the proportion between sizes, the length of the end part 62A of the front side wall part 62F is desired to be 10 to 40% of the length of the front side wall part 62F. In this embodiment, the end part 62A of the front side wall part 62F smoothly continues from the part of the front side wall part 62F other than the end part 62A to have a surface on the front side as a curved surface with a curvature radius of 0.14 mm, but is not limited thereto. The curvature radius of the end part 62A's surface on the front side (outer side) can be selected from a wide range of 0.05 to 2.0 mm or a preferable range of 0.10 to 1.0 mm.

Symmetrically, the length of the end part 62SA of the symmetrical front side wall part 63SF is approximately 20% of the length of the symmetrical front side wall part 63SF, but is not limited thereto. As for the proportion between sizes, the length of the end part 63SA of the symmetrical front side wall part 63SF is desired to be 10 to 40% of the length of the symmetrical front side wall part 63SF. In this embodiment, the end part 63SA of the symmetrical front side wall part 63SF smoothly continues from the part of the symmetrical front side wall part 63SF other than the end part 63SA to have a surface on the rear side as a curved surface with a curvature radius of 0.14 mm, but is not limited thereto. The curvature radius of the end part 63ST's surface on the rear side (outer side) can be selected from a wide range of 0.05 to 2.0 mm or a preferable range of 0.10 to 1.0 mm.

Further, in this embodiment, the symmetrical curved surfaces 62T and 63ST of the back side wall part 62B are both formed as a curved surface with a curvature radius of 0.40 mm, but is not limited thereto. The curvature radius can be selected from a wide range of 0.05 to 2.0 mm or a preferable range of 0.10 to 1.0 mm.

The above-described tissue ligating device 60 of the sixth embodiment can also be used according to a method of usage similar to the method explained referring to FIGS. 4 to 10.

Here, in the tissue ligating device 60 in this embodiment, a part of the back side wall part 62B farther from the curved wall part 62C than the end part of the front side wall part 62F far from the curved wall part 62C has the surface 62T inclined towards the front side. The end part 62A of the front side wall part 62F far from the curved wall part 62C is inclined towards the front side. With these features, the procedure of guiding the suture thread 80 to the region between the back side wall part 62B and the front side wall part 62F is very easy.

A part of the back side wall part 62B farther from the symmetrical curved wall part 62SC than the end part of the symmetrical front side wall part 62SF far from the symmetrical curved wall part 62SC has the surface 63ST curved towards the back side. The end part 63SA of the symmetrical front side wall part 63SF far from the symmetrical curved wall part 63SC is also curved towards the back side. With these features, the procedure of guiding the suture thread 80 to the region between the back side wall part 62B and the symmetrical front side wall part 63SF is also very easy.

Further, according to this embodiment, with the existence of the rising surfaces 62S and 63SS, even when the suture thread 80 is going to leave the region between the back side wall part 62B and the front side wall part 62F or the region between the back side wall part 62B and the symmetrical front side wall part 63SF due to its elasticity or the like, the occurrence of such leaving is advantageously prevented.

Furthermore, according to this embodiment, postural stability of the tissue ligating device 60 is improved since the structure of the second fixation part 62 and that of the third fixation part 63 are symmetrical to each other. Operability is extremely high since both the second fixation part 62 and the third fixation part 63 are usable for the fixation of the suture thread 80.

Moreover, according to this embodiment, the part of the front side wall part 62F other than the end part 62A and the part of the symmetrical front side wall part 63SF other than the end part 63SA are both formed in a shape like a flat plate, and thus the procedure of crimping and deforming these parts and newly fixing a part of the suture thread 80 is also very easy.

DESCRIPTION OF REFERENCE CHARACTERS

10: Tissue ligating device of the first embodiment
11: First fixation part
12: Second fixation part
12F: Front side wall part
12T: Inclined end part
12B: Back side wall part
12C: Curved wall part
12S: Step part
13: Third fixation part
13SF: Symmetrical front side wall part
13SC: Symmetrical curved wall part
13ST: Inclined end part
13SS: Step part
20: Tissue ligating device of the second embodiment
21: First fixation part
22: Second fixation part
22F: Front side wall part
22T: Curved end part
22B: Back side wall part
22C: Curved wall part
22S: Step part
23: Third fixation part
23SF: Symmetrical front side wall part
23SC: Symmetrical curved wall part
23ST: Symmetrical curved end part
23SS: Step part
30: Tissue ligating device of the third embodiment
31: First fixation part
32: Second fixation part
32F: Front side wall part
32C: Curved wall part
32B: Back side wall part
32T: Inclined surface
33: Third fixation part
33SF: Symmetrical front side wall part
33SC: Symmetrical curved wall part
33ST: Inclined surface
40: Tissue ligating device of the fifth embodiment
41: First fixation part
42: Second fixation part
42F: Front side wall part
42C: Curved wall part
42B: Back side wall part
42S: Rising surface
42T: Inclined surface
43: Third fixation part
43SF: Symmetrical front side wall part
43SC: Symmetrical curved wall part
43SS: Rising surface
43ST: Inclined surface
50: Tissue ligating device of the fifth embodiment
51: First fixation part
52: Second fixation part
52F: Front side wall part
52A: Inclined end part
52C: Curved wall part
52B: Back side wall part
52S: Rising surface
52T: Inclined surface
53: Third fixation part
53SF: Symmetrical front side wall part
53SA: Inclined end part
53SC: Symmetrical curved wall part
53SS: Rising surface
53ST: Inclined surface
60: Tissue ligating device of the sixth embodiment
61: First fixation part
62: Second fixation part
62F: Front side wall part
62A: Curved end part
62C: Curved wall part
62B: Back side wall part
62S: Rising surface
62T: Curved surface
63: Third fixation part
63SF: Symmetrical front side wall part
63SA: Curved end part
63SC: Symmetrical curved wall part
63SS: Rising surface
63ST: Curved surface
80: Suture thread
81: Base end part
82: Suture needle
100: Tissue ligating device of JP2012130669A
101: First fixation part
102: Second fixation part
102F: Front side wall part
102B: Back side wall part
102C: Curved wall part
103: Third fixation part
103SF: Symmetrical front side wall part
103SC: Symmetrical curved wall part
200: Suture thread
201: Base end part
202: Suture needle

The invention claimed is:

1. A tissue ligating device used for ligating tissue, comprising:
a first fixation part configured to allow a base end part of a suture thread to be fixed thereto; and
a second fixation part configured to allow insertion of the suture thread therethrough and allow to be crimped so as to newly fix a part of the suture thread, and thereby to define a loop starting from the base end part, in a state after ligation of tissue is performed,
wherein:
the second fixation part includes a back side wall part, a front side wall part, and a curved wall part turning back from the back side wall part to the front side wall part,
the back side wall part is longer than the front side wall part, and
a first part of the back side wall part farther from the curved wall part than an end part of the front side wall part far from the curved wall part has a rising surface that extends straightly towards the front side wall part and an inclined surface continuing to the rising surface and inclined or curved away from the rising surface, the inclined surface being farther away from the curved wall part than the rising surface.

2. The tissue ligating device according to claim 1, wherein:
a second part of the back side wall part closer to the curved wall part than the rising surface extends straightly in a plan view, and
the inclined surface of the back side wall part is inclined with respect to the second part of the back side wall part by an angle in a range of 10 to 80 degrees.

3. The tissue ligating device according to claim 1, wherein:
back side wall part includes a curved surface, such that it has an arc-like cross section,
a second part of the back side wall part closer to the curved wall part than the rising surface extends straightly in a plan view, and
a curvature radius of the arc-like cross section of the curved surface of the back side wall part is in a range of 0.05 to 2.0 mm.

4. The tissue ligating device according to claim 1, further comprising a third fixation part configured to allow insertion of the suture thread therethrough and allow to be crimped so as to newly fix a part of the suture thread, and thereby to define a loop starting from the base end part, in a state after ligation of tissue is performed,
wherein:
the third fixation part includes a symmetrical front side wall part that is symmetrical to the front side wall part of the second fixation part with respect to the back side wall part of the second fixation part and a symmetrical curved wall part turning back from the back side wall part to the symmetrical front side wall part,
the back side wall part is longer than the symmetrical front side wall part, and
a part of the back side wall part farther from the symmetrical curved wall part than an end part of the symmetrical front side wall part far from the symmetrical curved wall part has a surface inclined or curved towards a back side.

5. The tissue ligating device according to claim 1, wherein the first fixation part is configured to allow a part of the suture thread to be fixed thereto as the base end part through insertion of the suture thread and crimping in a state before ligation of tissue is performed.

6. The tissue ligating device according to claim 1, further comprising a suture thread attached to the first fixation part.

7. The tissue ligating device according to claim 6, wherein one end of the suture thread is provided with a suture needle.

8. The tissue ligating device according to claim 1, wherein:
a second part of the back side wall part closer to the curved wall part than the rising surface extends straightly in a first direction, in a plan view, and
the rising surface extends from an end of the second part in a second direction which is substantially perpendicular to the first direction, in the plan view.

9. A tissue ligating device comprising:
a first fixation part having a space configured to allow insertion of a suture thread therethrough and configured to be crimped so as to fix a base part of the suture thread;
a second fixation part having a space configured to allow insertion of the suture thread therethrough and configured to be crimped so as to fix another part of the suture thread; and
a third fixation part having a space configured to allow insertion of the suture thread therethrough and configured to be crimped so as to fix yet another part of the suture thread;
wherein:
the first fixation part comprises a first part of a back side wall part, the back side wall part extending along a central axis extending in a first direction;
the second fixation part comprises a second part of the back side wall part,
a front side wall part, and a curved wall part turning back from the back side wall part to the front side wall part;
the third fixation part comprises the second part of the back side wall part,
a front side wall part, and a curved wall part turning back from the back side wall part to the front side wall part;
the second part of the back side wall part has a smaller width than the first part of the back side wall part measured in a second direction perpendicular to the first direction;
the first part of the back side wall part has a first surface extending in the second direction, and the second part of the back side wall part is connected to the first surface to define rising surfaces rising from side surfaces of the second part of the back side wall part; and
the first part of the back side wall part has side surfaces continuing to the rising surfaces, wherein the side surfaces of the first part of the back side wall part incline or curve away from the central axis of the back side wall part as the side surfaces of the first part of the back side wall part extend away from the rising surfaces.

10. The tissue ligating device according to claim 9, wherein said tissue ligating device is symmetric with respect to the central axis of the back side wall part.

* * * * *